(12) United States Patent
VanVeggel et al.

(10) Patent No.: US 8,647,604 B2
(45) Date of Patent: Feb. 11, 2014

(54) LANTHANIDE RICH NANOPARTICLES, AND THEIR INVESTIGATIVE USES IN MRI AND RELATED TECHNOLOGIES

(75) Inventors: Franciscus C. J. M. VanVeggel, British Columbia (CA); Robert Scott Prosser, Ontario (CA); Cunhai Dong, British Columbia (CA)

(73) Assignee: UVic Industry Partnerships Inc., Victoria, British Columbia (CA)

( * ) Notice: Subject to any disclaimer, the term of this patent is extended or adjusted under 35 U.S.C. 154(b) by 0 days.

(21) Appl. No.: 11/627,273

(22) Filed: Jan. 25, 2007

(65) Prior Publication Data

US 2007/0218009 A1  Sep. 20, 2007

Related U.S. Application Data

(60) Provisional application No. 60/762,464, filed on Jan. 25, 2006.

(51) Int. Cl.
*A61B 5/055* (2006.01)

(52) U.S. Cl.
USPC .......................................... 424/9.34

(58) Field of Classification Search
None
See application file for complete search history.

(56) References Cited

U.S. PATENT DOCUMENTS

| | | | |
|---|---|---|---|
| 5,581,398 A | 12/1996 | van Veggel et al. | |
| 5,657,156 A | 8/1997 | van Veggel et al. | |
| 6,180,029 B1 | 1/2001 | Hampden-Smith et al. | |
| 6,534,039 B2 * | 3/2003 | Hainfeld | 424/9.32 |
| 2003/0032192 A1 | 2/2003 | Haubold et al. | |
| 2005/0260137 A1 * | 11/2005 | Acar et al. | 424/9.34 |
| 2007/0274664 A1 | 11/2007 | van Veggel et al. | |

FOREIGN PATENT DOCUMENTS

| | | | |
|---|---|---|---|
| CA | 2201750 | 4/1996 | |
| WO | WO 2004/085571 | 10/2004 | |
| WO | WO 2004085571 A1 * | 10/2004 | C09K 11/77 |

OTHER PUBLICATIONS

Thunus et al., Coordination Chemistry Reviews, 1999, 184, 125-155.*
Citric acid MSDS, 3 pages.*
"Written Opinion of the International Searching Authority," from International Application No. PCT/CA2004/000447, filed Mar. 24, 2004. 6 pages.
"International Search Report," from International Application No. PCT/CA2004/000447, filed Mar. 24, 2004. 3 pages.
Office Action dated Jun. 30, 2008, in U.S. Appl. No. 10/550,573 (Publ. No. US 2007-0274664 A1).

* cited by examiner

*Primary Examiner* — Kyle Purdy

(74) *Attorney, Agent, or Firm* — Klarquist Sparkman, LLP

(57) ABSTRACT

An aqueous soluble, lanthanide rich nanoparticle for investigative use, such as NMR, MRI, CT, PET, and GdNCT is provided. The nanoparticle is synthesized from a mixture comprising lanthanide ions and coated with a suitably selected organic ligand such that the resultant nanoparticle is soluble in aqueous solutions. A method of collecting nuclear magnetic resonance information on a sample or a subject is also provided.

24 Claims, 5 Drawing Sheets

US 8,647,604 B2

Figure 1A:
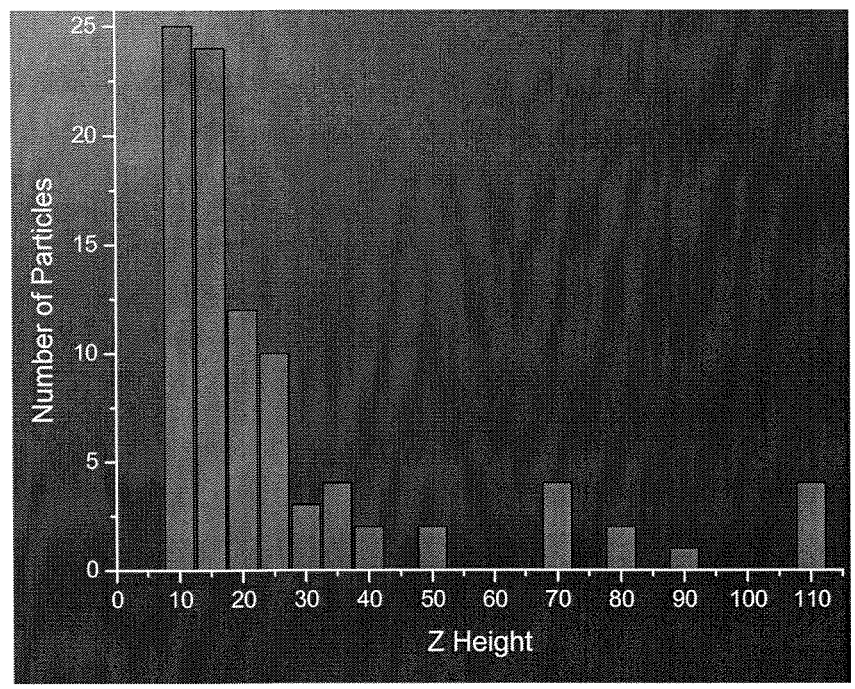

LANTHANIDE RICH NANOPARTICLES, AND THEIR INVESTIGATIVE USES IN MRI AND RELATED TECHNOLOGIES

CROSS REFERENCE TO RELATED APPLICATIONS

This application claims benefit of U.S. Provisional Patent Application No. 60/762,464 filed Jan. 25, 2006 and entitled "LANTHANIDE RICH NANOPARTICLES AND METHOD FOR THEIR USE IN IMAGING TECHNOLOGIES," which is hereby incorporated herein by reference.

FIELD

The present technology relates to a new class of water soluble paramagnetic agent consisting of lanthanide rich nanoparticles. More specifically, the technology relates to the use of this new class of water soluble paramagnetic agents in investigative imaging technologies and molecular characterization.

BACKGROUND

In the proteomics era, minimizing the time required to perform the necessary NMR assignment and structure studies is key to progress. Such studies often require months of NMR time for protein molecular weights in excess of 30 kDa. Moreover, strategies aimed at streamlining studies of large proteins and macromolecular complexes include the use of higher magnetic fields and partial deuteration. Consequently, spin-lattice relaxation times ($T_1$) become inordinately long and sensitivity (or time) is compromised. Paramagnetic relaxation agents may be used to quench solvent $T_1$'s, without undue line broadening of protein resonances. If $T_1$ of water is sufficiently low, a considerable reduction of $^1H$ relaxation times is expected to occur on the surface and even the interior of the protein through water exchange and spin-diffusion. In flow-through NMR one of the most serious limitations to sensitivity is the polarization time (ie the sample will become polarized over a timescale comparable to $3 \times T_1$, which is often far less than the time a sample spends in the magnet). As a result, NMR is frequently the bottleneck in tandem imaging techniques such as tandem HPLC/Mass Spectroscopy/flow NMR methods. Paramagnetic relaxation agents are equally important in Magnetic Resonance Imaging (MRI), since relatively small quantities can be safely introduced intravenously or orally, resulting in significant spin-lattice relaxation or $T_1$ effects in certain tissues. Differences in $T_1$ effects in neighboring tissues give contrast in MRI images, particularly when pulse sequences are employed in which differences in $T_1$ are exploited. A second means of enhancing contrast by MRI is by so-called T2-imaging. This requires relaxation or contrast agents which contribute to local changes in susceptibility or T2 (spin-spin relaxation times).

Paramagnetic Relaxation Agents and MRI Contrast Agents

Conventional paramagnetic relaxation agents are generally not used in NMR applications due to: 1) weak association of certain regions of the protein with the agent (for example a $Gd^{3+}$ chelate), 2) severe line broadening, and 3) difficulty of later separating the sample from the paramagnetic additive.

In theory, $Gd^{3+}$ is a good paramagnetic relaxation agent because of its large magnetic moment and ns-timescale electronic spin relaxation rates. Simple $Gd^{3+}$-chelates such as EDTA, DTPA, or DOTA are routinely used as paramagnetic relaxation agents in NMR studies. However, there are numerous shortcomings. Firstly, the chelated gadolinium ion may coordinate with the carboxyl ligands of the chelate, with water, and to some extent, with regions of partial charge on the protein, thereby excessively shifting and broadening some protein resonances and obscuring assignments. Secondly, rapid tumbling of a small chelate such as $Gd^{3+}$:EDTA, $Gd^{3+}$:DTPA, or $Gd^{3+}$:DOTA diminishes the effectiveness of the relaxation agent, since the correlation time, $\tau_{eff}$, associated with paramagnetic relaxation, is a function of the average tumbling time of the $Gd^{3+}$ chelate, $\tau_c$, and the electronic relaxation time of the paramagnet, $T_{1e}$, such that $$1/\tau_{eff} = 1/\tau_c + 1/T_{1e}.$$

In order to overcome this deficiency, a wide variety of slow-tumbling water soluble complexes that bind several to many $Gd^{3+}$ ions have been designed, primarily for purposes of obtaining enhanced bulk water relaxation in Magnetic Resonance Imaging (MRI) applications. In this case, the $Gd^{3+}$ complexes dramatically decrease bulk relaxation times and so-called $T_1$-weighted images may reveal improved contrast, depending on the partitioning properties of the contrast agent into adjacent tissues or cells. Such complexes include zeolites,[i] micellar aggregates,[ii] polyaminoacids,[iii] polysaccharides,[iv] and dendrimers.[v,vi] While these complexes are useful for specific $T_1$-weighted MRI applications in certain tissues, many of these materials would be problematic as relaxation agents in high throughput NMR or NMR studies of proteins due to nonspecific binding between chelate and the molecule of interest and background signal from the agent. Furthermore, although the majority of NMR experiments in assignment studies may benefit from a relaxation agent, others such as long-range NOESY distance measurements, or relayed experiments which require long lived coherences, may perform worse with the addition of relaxation agents. Consequently, in NMR experiments, it is highly desirable that the relaxation agent can be reliably and rapidly removed and the molecule under study easily retrieved. In MRI imaging experiments it is also important that the contrast agent also be removed. Nanoparticles of 50 nm diameters or smaller, are routinely removed via the reticuloendothelial system and ultimately excreted via the bile.[vii, viii, ix]

Basic Physical Features of the $GdF_3$ and $LaF_3/GdF_3$ Nanoparticles

Nanoparticles have found many uses in wide ranging fields of materials chemistry, including catalysts, energy storage, packaging and textiles, and advanced computing. In the health science industry, nanoparticles are used both as detection and delivery agents. For example, hydrophobic antitumor drugs can be packaged within nanoparticle matrices that commonly take the form of inorganic or organic polymers, proteins or antibodies, dendrimers, or liposomes. In some cases, the nanoparticle may be functionalized for targeting to a specific tissue or cell, by additional ligation. For example, coatings such as lipopolysaccharides are frequently added to control drug release, endosomal uptake, and bioactivity.

There is a need for contrast and relaxation agents that have the following attributes.

1) Strong relaxation effects without undue broadening. The electronic relaxation time should be on the nanosecond timescale and the paramagnetic complex should be large enough to inhibit excessively fast tumbling. In MRI, strong ($T_1$) relaxation effects are also desired.

2) High solubility. This helps to extend the upper limits of concentration and thus contrast in MRI, while relaxation effects in NMR also depend on concentration. The particles can also be readily prepared to be soluble in a wide variety of solvents.

3) Can be readily functionalized and with a multitude of groups. Dendrimers, zeolites, and polypeptides, for example, can be problematic if multiple ligands are needed. In MRI multiple groups could be envisaged to assist in directing a contrast agent to a target tissue, providing proper charge or solubility, controlling immune responses by appropriate coatings such as PEG, and ligating attached drugs for subsequent release.

4) Do not exhibit leaching effects. Traditional lanthanide chelates will leach (leak) $Gd^{3+}$ ions over time. Since $Gd^{3+}$ is toxic this is an obvious limitation for MRI. In NMR, this is a limitation because free lanthanides may then bind to the protein or molecule of interest.

5) Can be easily retrieved or removed. Centrifugation or ultracentrifugation are often used to separate or fractionate particles of different densities. Dialysis can be used to size fractionate particles. Other techniques such as binding agents, including, for example, but not limited to antibodies, and biotin can be used to extract particles by first coating the particle with antigen and avidin, respectively.

It is an object of the present technology to overcome the deficiencies in the prior art.

SUMMARY

There is a need for contrast and relaxation agents that give larger contrasts, have lower toxicities, can be easily functionalized, do not exhibit leaching effects and can be easily removed from the sample or subject. The present technology provides such compounds. The nanoparticle are synthesized from a mixture comprising lanthanide ions and coated with a suitably selected organic ligand such that the resultant nanoparticle is soluble in aqueous solutions. The resulting nanoparticles are for investigative use.

In one aspect the lanthanide ions are selected from the group consisting of Ce, Pr, Nd, Sm, Eu, Gd, Tb, Dy, Ho, Er, Tm, Yb, La, Lu, and Y.

In another aspect the organic ligands are independently selected from the group consisting of carboxylic acids and their esters, organo phosphorous compounds and their esters, phosphonates and phosphine oxides, alcohols, thiols, sulfoxides, sulfones, ketones, aldehydes, the group consisting of polymers of carboxylic acids and their esters, organo phosphorous compounds and their esters, phosphonates and phosphine oxides, alcohols, thiols, sulfoxides, sulfones, ketones, aldehydes the group consisting of and alkyl ammonium compounds ($RNH_3^+$, $R_1R_2NH_2^+$, $R_1R_2R_3NH^+$, $R_1R_2R_3R_4N^+$, where R is independently selected from alkyl and aromatic groups.

In another aspect, the ligands are selected from the group consisting of citrate, biotin, amino acids, $H_3N^+CH_2CH_2OPO_3^{2-}$.

In another aspect, the ligands are surface modified.

In another aspect, the mixture comprises at least two lanthanide ions.

In another aspect, the at least two lanthanide ions are $Gd^{3+}$ and $La^{3+}$.

In another aspect, the mixture comprises gadolinium fluoride and lanthanum fluoride.

In another aspect, the mixture comprises at least 50% gadolinium fluoride.

In another aspect, the mixture comprises at least 80% gadolinium fluoride.

In another aspect, the organic ligand is citrate or $H_3N^+CH_2CH_2OPO_3^{2-}$.

In another aspect, the lanthanide ion is gadolinium ion.

In another aspect, the lanthanide ion is provided as gadolinium fluoride.

In another aspect, the nanoparticles range in size from about 10 to about 150 nm in diameter.

In another aspect, the nanoparticles range in size from about 10 to about 20 nm in diameter.

In another aspect, the organic ligand is citrate.

In another aspect, the nanoparticles range in size from about 5 to about 10 nm in diameter.

In another aspect, the nanoparticle is a core shell nanoparticle.

In another aspect, the nanoparticle is a core nanoparticle.

In another embodiment, a method of collecting nuclear magnetic resonance information on a subject or a sample is provided. The method comprises synthesizing aqueous soluble lanthanide rich nanoparticles, labeling the subject or the sample with the nanoparticles, and collecting the nuclear magnetic resonance information.

In one aspect of the method, the nuclear magnetic resonance information is magnetic resonance images.

In another aspect of the method, the subject is a living subject.

In another aspect of the method, the living subject is a human.

In another aspect of the method, the nuclear magnetic resonance information is nuclear magnetic resonance spectra.

In another aspect of the method, the sample is in a solution.

In another aspect, the method further comprises recovering the sample by density separation methods.

In another aspect of the method, the density separation methods are centrifugation methods.

In another aspect of the method, the sample is a protein sample.

In another embodiment, a method of collecting tomography information on a subject or a sample is provided. The method comprises synthesizing aqueous soluble lanthanide rich nanoparticles, labeling the subject or the sample with said nanoparticles, and collecting said tomography information.

In another aspect of the method, the nanoparticles are synthesized from a mixture comprising lanthanide ions and coated with a suitably selected organic ligand such that the resultant nanoparticles are soluble in aqueous solutions.

In another aspect of the method the lanthanide ions are selected from the group consisting of Ce, Pr, Nd, Sm, Eu, Gd, Tb, Dy, Ho, Er, Tm, Yb, La, Lu, and Y.

In another aspect of the method the organic ligands are independently selected from the group consisting of carboxylic acids and their esters, organo phosphorous compounds and their esters, phosphonates and phosphine oxides, alcohols, thiols, sulfoxides, sulfones, ketones, aldehydes, the group consisting of polymers of carboxylic acids and their esters, organo phosphorous compounds and their esters, phosphonates and phosphine oxides, alcohols, thiols, sulfoxides, sulfones, ketones, aldehydes the group consisting of and alkyl ammonium compounds ($RNH_3^+$, $R_1R_2NH_2^+$, $R_1R_2R_3NH^+$, $R_1R_2R_3R_4N^+$, where R is independently selected from alkyl and aromatic groups.

In another aspect of the method the ligands are selected from the group consisting of citrate, biotin, amino acids, $H_3N^+CH_2CH_2OPO_3^{2-}$.

In another aspect of the method the ligands are surface modified.

In another aspect of the method, the mixture comprises at least $Gd^{3+}$.

In another aspect of the method, the $Gd^{3+}$ is gadolinium fluoride.

In another aspect of the method, the mixture further comprises $La^{3+}$.

In another aspect of the method, the $La^{3+}$ is lanthanum fluoride.

In another embodiment, a method of collecting tomography information on a subject or a sample is provided. The method comprises synthesizing aqueous soluble lanthanide rich nanoparticles, labeling the subject or the sample with said nanoparticles, and collecting said tomography information.

In another aspect of the method the tomography is positron emission tomography.

In another aspect of the method the tomography is computed tomography.

In another embodiment, a use of aqueous soluble gadolinium-rich nanoparticle for gadolinium neutron capture therapy is provided.

In one aspect of the use, the nanoparticles are coated with a suitably selected organic ligand such that the resultant nanoparticles are soluble in aqueous solutions.

In another aspect of the use, the organic ligands are independently selected from the group consisting of carboxylic acids and their esters, organo phosphorous compounds and their esters, phosphonates and phosphine oxides, alcohols, thiols, sulfoxides, sulfones, ketones, aldehydes, the group consisting of polymers of carboxylic acids and their esters, organo phosphorous compounds and their esters, phosphonates and phosphine oxides, alcohols, thiols, sulfoxides, sulfones, ketones, aldehydes the group consisting of and alkyl ammonium compounds ($RNH_3^+$, $R_1R_2NH_2^+$, $R_1R_2R_3NH^+$, $R_1R_2R_3R_4N^+$, where R is independently selected from alkyl and aromatic groups.

In another aspect of the use, the ligands are selected from the group consisting of citrate, biotin, amino acids, $H_3N^+CH_2CH_2OPO_3^{2-}$.

In another aspect of the use, the ligands are surface modified.

In another aspect of the use, the mixture comprises at least $Gd^{3+}$.

In another aspect of the use, the $Gd^{3+}$ is gadolinium fluoride.

In another aspect of the use, the mixture further comprises $La^{3+}$.

In another aspect of the use, the $La^{3+}$ is lanthanum fluoride.

In another aspect of the use, the organic ligand is either citrate or $H_3N^+CH_2CH_2OPO_3^{2-}$.

In another aspect, the lanthanide ions are selected from the group consisting of wherein said lanthanide is selected from the group consisting of La, Dy, Ho, and Gd.

In another aspect of the method, the lanthanide ions are selected from the group consisting of wherein said lanthanide is selected from the group consisting of La, Dy, Ho, and Gd.

FIGURE DESCRIPTIONS

FIG. 1. Atomic Force Microscopy images of nanoparticles, consisting of: A. An 80/20 mixture of $GdF_3$ and $LaF_3$, surface functionalized with positively charged ammonium acetate groups, and B. $GdF_3$, surface functionalized with negatively charged citric acid groups in accordance with an embodiment. The histograms, in each system, reveal a broad distribution of particle sizes, with typical cross sectional diameters of 51.5 nm for the 80/20 $GdF_3$/$LaF_3$ particles and 129.3 nm for the $GdF_3$ particles, as determined by dynamic light scattering measurements.

Figure 2:
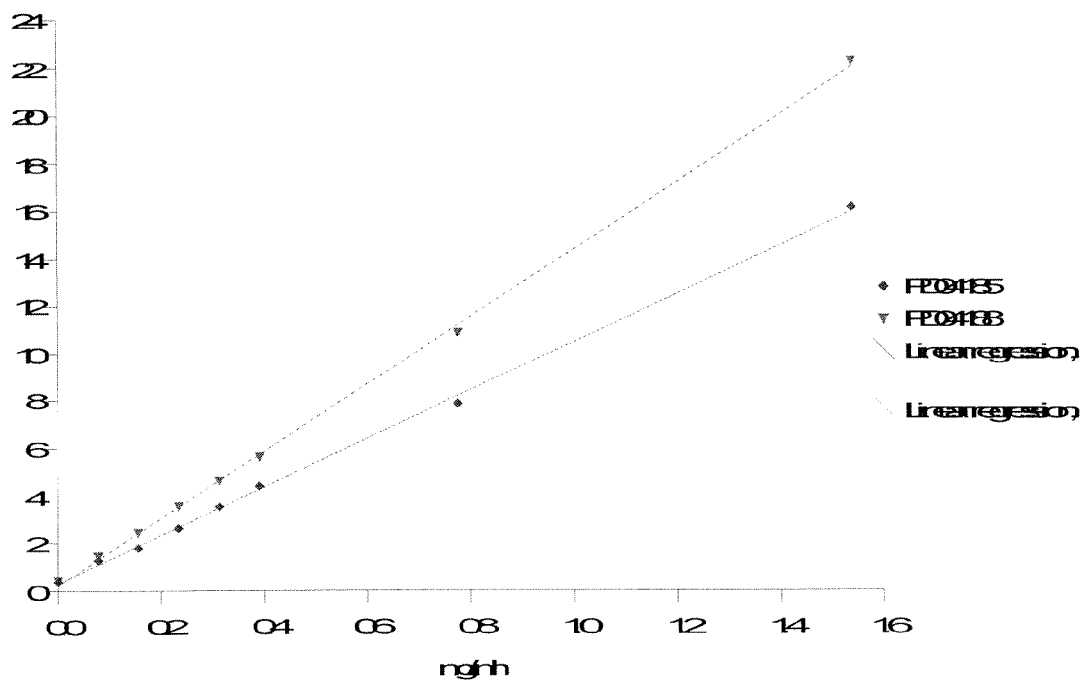

FIG. 2. $^1H$ spin-lattice relaxation rates of $H_2O$ versus mass concentration (mg/ml) of either $GdF_3$ (red) or $GdF_3$/$LaF_3$ (blue) nanoparticles in a 90/10 $H_2O$/$D_2O$ mixture.

Figure 3:
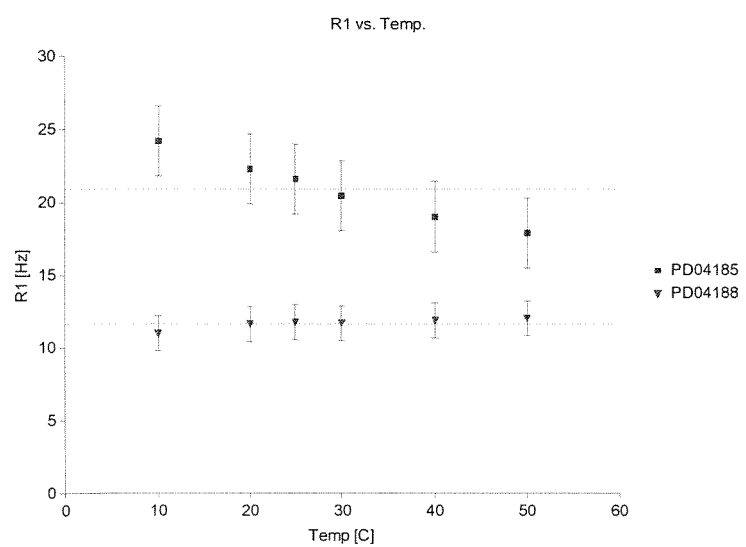

FIG. 3. Temperature dependence of the spin lattice relaxation rates of water for $GdF_3$ and the 80/20 $GdF_3$/$LaF_3$ nanoparticles, at a concentration of 1.53 mg/ml and at 600 MHz $^1H$ Larmor frequency.

Figure 4:
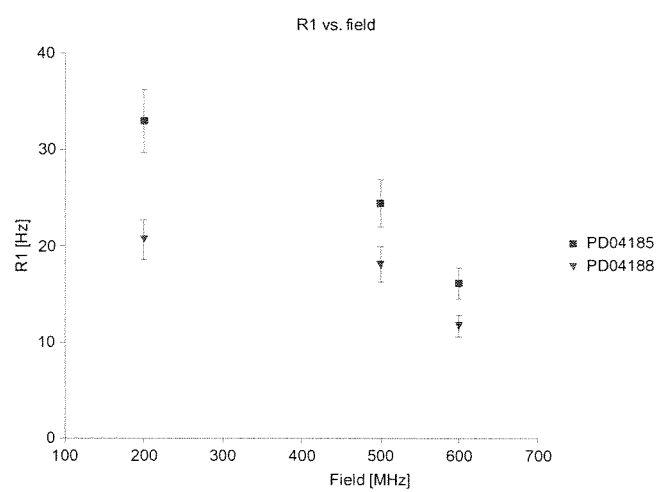

FIG. 4. Field dependence of the spin lattice relaxation rates of water for $GdF_3$ and the 80/20 $GdF_3$/$LaF_3$ nanoparticles, at a concentration of 1.5 mg/ml and at 20° C.

Figure 5:
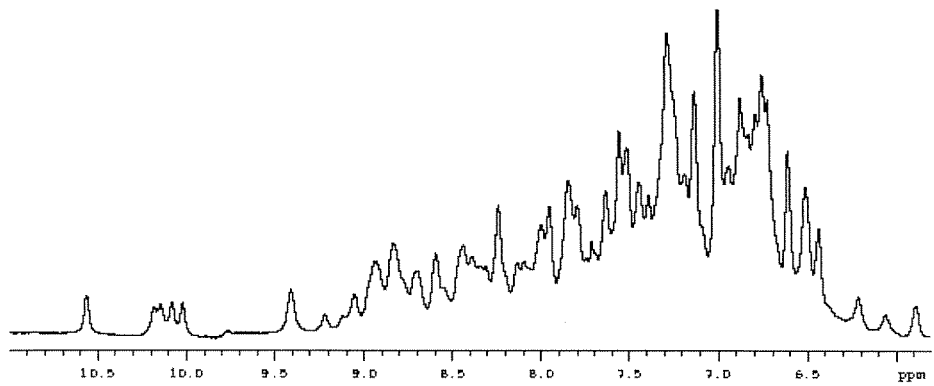
Figure 5:
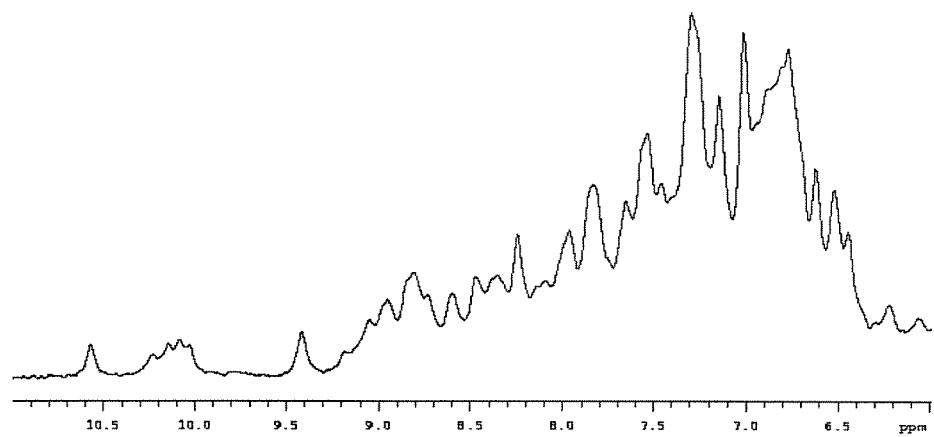

FIG. 5. 600 MHz $^1H$ NMR spectrum of 1 mM lysozyme in a 90/10 buffered solution, containing no paramagnetic additives (A), and 10 nM nanoparticles (B). All spectra were recorded, using a WATERGATE solvent suppression sequence at a temperature of 25° C.

DETAILED DESCRIPTION

Definitions:

Nanoparticles: The term "nanoparticles" as used herein, can also refer to nanoclusters, clusters, particles, dots, quantum dots, small particles, and nanostructured materials. When the term "nanoparticle" is used, one of ordinary skill in the art will appreciate that this term encompasses all materials with small size and often associated with quantum size effects, generally the size is less than 100 nm. Nanoparticles can comprise a core or a core and a shell, as in core-shell nanoparticles.

Lanthanides: The term "lanthanide" as used herein refers to Ce, Pr, Nd, Sm, Eu, Gd, Tb, Dy, Ho, Er, Tm, Yb, La, combinations thereof, compounds containing Ce, Pr, Nd, Sm, Eu, Gd, Tb, Dy, Ho, Er, Tm, Yb, La and combinations thereof, and ions of Ce, Pr, Nd, Sm, Eu, Gd, Tb, Dy, Ho, Er, Tm, Yb, La and combinations thereof. Ionic states ranging from +2 to +4 are contemplated.

Surface modifications: Surface modification of the ligands that are on the surface of the nanoparticles involves altering the chemical and/or biological properties of the ligands. For example, but not to be limiting, we have shown for $Eu^{3+}$, $Er^{3+}$, and $Nd^{3+}$ doped nanoparticles that had $H_3N^+CH_2CH_2OPO_3^{2-}$ as stabilizing ligands can be surface modified with, for example, activated esters, including activated esters with polyethylene glycol (the phosphate group binds to the surface of the nanoparticles and the amino group is reacted with the activated ester).

CT: Computed tomography.
MRI: Magnetic resonance imaging.
NMR: Nuclear magnetic resonance.
PET: Positron Emission Tomography
GdNCT: Gadolinium neutron capture therapy Investigative uses: CT, PET, MRI and NMR and related technologies for obtaining at least one of structural, physiological, morphological and chemical information about a sample or subject and GdNCT for investigative therapy of a subject.

Tandem imaging: X-ray imaging (Computed tomography or CT) and PET scanning, or X-ray imaging (Computed tomography or CT) and MRI are examples of tandem imaging. Tandem imaging in general is the utilization of two or more investigative imaging techniques.

Ligands: All ligands may have one or more functional group independently selected from the following:
Carboxylic acids and their esters;
Organo phosphorous compounds (phosphonic and phosphinic acids and their esters), phosphonates, phosphine oxides;
Alcohols;

Thiols;
Sulfoxides;
Sulfones;
Ketones;
Aldehydes;
Polymers of the above listed ligands; and
Alkyl ammonium compounds ($RNH_3^+$, $R_1R_2NH_2^+$, $R_1R_2R_3NH^+$, $R_1R_2R_3R_4N^+$, with Rx=alkyl or aromatic substituent).

Nanoparticle: All nanoparticles may have one or more Ln independently selected from the above list and comprise at least one of:

$LnX_3$ (X=F,Cl,Br,I)
$Ln_2X_3$ (X=O, S, Se, Te)
$Ln_2XxYy$ (X=O, S, Se, Te; Y=O, S, Se, Te)
$Ln_2X_3$ (X=$CO_3$, $C_2O_4$, $SO_4$, $SO_3$)
$LnX$ (X=$PO_4$, $PO_3$, $VO_4$)
Borates
Aluminates
Gallates
Silicates
Germanates
Niobates
Tantalates
Wolframates
Molybdates
Nitrides
$XO_2$ (X=Ti, Zr, Hf, Ge, Sn, Pb)
XO (X=Ge, Sn, Zn, Pb, Cd, Hg)
$X_2O_5$ (X=V, Nb, Ta)
$X_2O_3$ (X=Al, Ga, In)

DESCRIPTION

Results of physical characterizations and NMR relaxation studies of solubilized nanoparticles prepared from $GdF_3$ or a mixture of 80% $GdF_3$ and 20% $LaF_3$ show that high aqueous solubilities were achieved by coating the particles with ligands of either negatively charged citrate groups ($GdF_3$ particles) or positively charged ammonium groups (80/20 $GdF_3/LaF_3$). The sample with positive charges was made with the following ligand: $H_2NCH_2CH_2OPO_3H_2$ which will be at pH=6-7: $^+H_3NCH_2CH_2OPO_3^{2-}$, so the negatively charged group coordinates to the surface and the positive charges are on the surface of the nanoparticles as a whole and thus closest to the water (on average).

The high solubility and relaxivity, low background $^1H$ NMR signal, capacity to be functionalized with positive or negative surface charges, ease of removal, and ability to recover the sample from the supernatant (vide infra), demonstrates that the $GdF_3$ nanoparticles are useful as relaxation and contrast agents in NMR and MRI.

Example 1

1—$GdF_3:LaF_3$ (80/20) stabilized with 2-aminoethyl phosphate: A solution of 2-aminoethyl phosphate (0.14 g, 1.02 mmol) in 25 ml of water was neutralized with $NH_4OH_{(aq)}$, followed by the addition of NaF (0.13 g, 3.00 mmol). The solution was heated to 75° C. followed by the addition of $La(NO_3)_3 \cdot 6H_2O$ (0.12 g, 0.27 mmol) and $Gd(NO_3)_3 \cdot 6H_2O$ (0.48 g, 1.06 mmol) in 2 ml of water. The 2 ml solution was added drop-wise and stirred at 75° C. for 3-4 hrs, yielding a clear solution. Isolation of the particles was done by removing the water until the product was reduced to a paste-like consistency, which was then redissolved in 5 ml of water and precipitated with ~50 ml of acetone. The particles were then isolated by centrifugation, after which the supernatant was poured off. The remaining precipitate was then triturated with acetone, separated by centrifugation, and dried under reduced pressure.

2—$GdF_3$ stabilized with citric acid: A solution of citric acid (0.41 g, 2.13 mmol) in 25 ml of water was neutralized with $NH_4OH_{(aq)}$ followed by the addition of NaF (0.13 g, 3.00 mmol). The solution was heated to 75° C. followed by the addition of $Gd(NO_3)_3 \cdot 6H_2O$ (0.60 g, 1.33 mmol) in 2 ml of water. The 2 ml solution was added drop-wise and stirred at 75° C. for 3-4 hrs, yielding a clear solution. Isolation of the particles was done by removing the water until the product was reduced to a paste-like consistency. Particles were then redissolved in 5 ml of water and precipitated with ~100 ml of ethanol. The particles were then isolated by centrifugation, after which the supernatant was poured off. The remaining precipitate was then triturated with ethanol, separated by centrifugation, and dried under reduced pressure.

The $GdF_3$ and $GdF_3/LaF_3$ nanoparticle morphologies and sizes were characterized by dynamic light scattering and atomic force microscopy. Atomic force microscopy (AFM) was performed using a Thermomicroscope Explorer. Samples were deposited from a water suspension on a freshly cleaved mica substrate, in which the bulk of the water was subsequently desorbed via a piece of paper towel at the corner of the mica sheet. Dynamic light scattering (DLS) experiments were carried out on a Brookhaven Instruments photon correlation spectrometer equipped with a BI-200SM goniometer, a BI-9000AT digital autocorrelator, and a Melles Griot He—Ne Laser (632.8 nm) with maximum power output of 75 mW. All water and nanoparticle solutions were filtered through 0.45 μm Teflon syringe filters. Sample vials used for measurements were rinsed 3 times with the above filtered water. Final sample concentrations used were 0.5 mg·$ml^{-1}$. DLS experiments were measured with the viewing direction perpendicular to the incident light direction.

Example 2

Figure 1B:
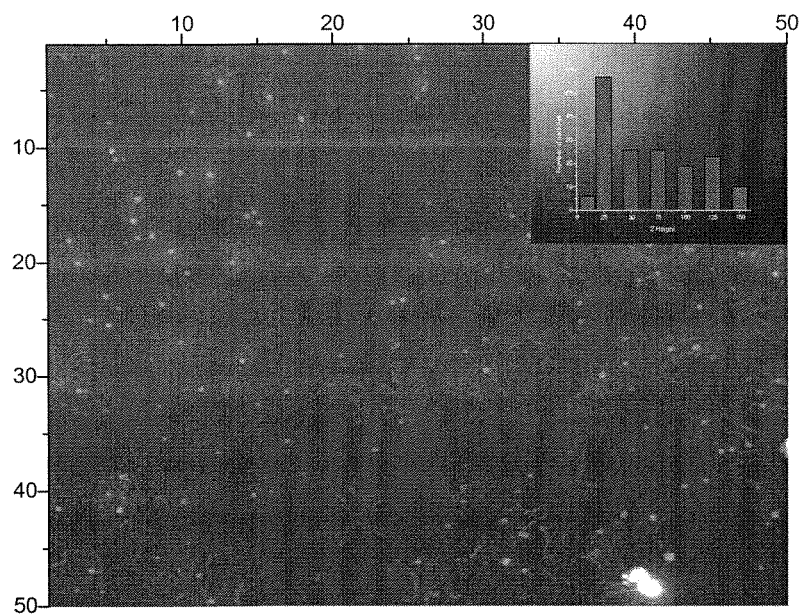

FIGS. 1A and 1B, obtained from atomic force microscopy, reveal broad distributions of particle sizes for nanoparticles prepared by method 1 or 2 above. In the case of the 80/20 ($GdF_3:LaF_3$) positive surface charge nanoparticles, atomic force measurements reveal a roughly bimodal size distribution with particle cross sections ranging from 10-50 nm and 80-110 nm, though sizes between 30 and 60 nm are more typical. The larger particles, in this case, are not suspected to consist of agglomerated particles from the 10-50 nm dimensions. An analysis of Dynamic light scattering measurements corroborate the size range estimated by AFM and suggest an effective diameter of 51.5 nm in $H_2O$ (average of 3 measurements), with an RMS error of $7.9 \times 10^{-2}$, with a size range matching that of the AFM distribution. The AFM-based size distribution of the nanoparticles made with $GdF_3$, stabilized with citric acid, are shown in FIG. 1B. Note that the size distribution suggests that particle sizes vary somewhat uniformly between 10 nm and 150 nm in diameter. An analysis of dynamic light scattering measurements gives an effective diameter of 129.3 nm in $H_2O$ (average of 3 measurements), with an RMS error of $5.7 \times 10^{-3}$, with a size range matching that of the AFM distribution. The larger particles are also expected to arise from growth formation, rather than particle agglomeration. The observation of slightly larger particle sizes with the GdF3 based nanoparticles is consistent with the observation that lanthanide solubilities typically decrease across the lanthanide series and the synthesis protocol results in slightly larger nanoparticles upon replacing $La^{3+}$ with $Gd^{3+}$. In fact, this was one of the motivating reasons for doping one of the nanoparticles (namely, the positive surface charged species) with $La^{3+}$, since solubility was significantly improved. Ultimately, control of size and solubility is important to targeting and retention times of nanoparticles in living systems. The size distribution profiles in FIG. 1 allow us to estimate the average particle weights, which are $8.6 \times 10^7$ Da and $1.4 \times 10^9$ Da for the positively charged $GdF_3/LaF_3$ and negatively charged $GdF_3$ nanoparticles, respectively.

FIG. 2 depicts the dependence of water spin-lattice relaxation rates as a function of increasing mass concentrations of each of the nanoparticles prepared by method 1 or 2, at 25° C. Based on the average particle weights, we can estimate the paramagnetic relaxation rates from the slopes of the relaxation rate profiles. The so-called molar relaxivities turn out to be $2.0 \times 10^7$ Hz/mmol and $8.8 \times 10^5$ Hz/mmol for the $GdF_3$ and 80/20 $GdF_3/LaF_3$ mixture. These relaxivities compare favorably to those obtained for $Gd^{3+}$ aggregates consisting of dendrimer cores, or the more recently developed zeolite shells used to sequester $Gd^{3+}$ for MRI studies of the stomach. It is probable that the bulk of the relaxation is coming from those $Gd^{3+}$ ions located on or near the surface since it is well known that relaxation is only conferred to bulk water if water is readily exchanging from the surface. Assuming typical cross sections of 129 nm and 51.3 nm for the two types of nanoparticles used in this study (ie $GdF_3$ possessing negatively charge citrate groups and 80/20 GdF3/LaF3 possessing positive surface charges, respectively) we can estimate that the mole fraction of Gd ions within the radius of water from the surface (~3 Å) is approximately 0.014 and 0.035, respectively.

FIG. 3 reveals the temperature dependence of the water spin-lattice relaxation rates of both nanoparticles of method 1 or 2 at concentrations of 1.53 and 1.54 mg/ml. For purposes of assessing the potential of the nanoparticles as MRI contrast agents, the relaxivities of both nanoparticles was also measured at additional available field strengths (200 MHz, 360 MHz, and 500 MHz). The result, shown in FIG. 4, reveals that the relaxivity is not strongly dependent on field strength between 200 and 600 MHz.

FIG. 5 compares $^1H$ NMR spectra of unlabeled lysozyme with varying amounts of nanoparticle added. Average amide spin-lattice relaxation times were observed to drop from 0.85 s to 0.25 s in the presence of only 15 nM 80/20 $GdF_3/LaF_3$ nanoparticles. This corresponds to an average paramagnetic rate of 2.5 Hz for the amide protons of lysozyme. Due to the positive net charge of the protein, the positively charged nanoparticles were chosen to minimize direct interactions between particles and the protein. A similar study was also performed with a small molecule (caffeine), labeled with nanoparticles, wherein the paramagnetic contribution to $^1H$ spin-lattice relaxation was between 3 and 5 Hz at 12 nM $GdF_3$ nanoparticle concentrations.

In MRI, it is preferable to remove the nanoparticles from the sample or subject.

While in living subjects it may be possible to direct the nanoparticles to the reticuloendothelial system, for subsequent excretion or removal via the bile, in other instances, the removal occurs in vivo. Hence, it is of note that in all cases, we observed that the nanoparticles could easily be removed by ultracentrifugation at 90,000 rpm for approximately 60 minutes, whereupon a light translucent gel was observed in the bottom of the centrifuge tube. Protein was simply extracted in the supernatant and subsequent NMR relaxation studies revealed that water relaxation rates returned to the relaxation rates associated with the paramagnetic-free sample.

Example 3

1—Preparation of AEP stabilized $GdF_3$:La(20%):Eu (0.5%) nanoparticles: A solution of 0.14 g of 2-aminoethyl dihydrogen phosphate in 25 mL of water was neutralized with ammonium hydroxide to a slightly acidic pH value of 5.08, 6.18 and 6.41, followed by addition of 0.126 g (3 mmol) of NaF. The solution was heated to 75° C. followed by the drop wise addition of a solution of $Gd(NO_3)_3$, $La(NO_3)_3$ and $Eu(NO_3)_3$ (a total of 3 mmol) in 2 ml of water. After stirring for 1 hour, particles were precipitated with ~100 mL of acetone, isolated by centrifugation, washed three times with acetone, followed by centrifugation, and dried under vacuum. Percentages are relative to the total amount of $Ln^{3+}$ ions.

2—Preparation of citrate stabilized $GdF_3$:Eu(x%, x=5 and 10) nanoparticles: A solution of 1 g of citric acid in 35 mL of water was neutralized with ammonium hydroxide to a pH of 6 followed by the addition of 0.126 g of NaF (3 mmol). The solution was heated to 75° C. followed by the drop wise addition of a solution of $Gd(NO_3)_3$ and $Eu(NO_3)_3$ (in total 1.33 mmol) in 2 mL of water. After stirring for 1 hour, particles were precipitated with ~50 mL of ethanol, isolated by centrifugation, washed three times with ethanol, followed by centrifugation, and dried under vacuum. Percentages are relative to the total amount of $Ln^{3+}$ ions.

3—Preparation of citrate stabilized $GdF_3$:Eu(x%, x=5 and 10)-$LaF_3$ core-shell nanoparticles: A solution of 2 g of citric acid in 35 mL of water was neutralized with ammonium hydroxide to a pH of 6 and heated to 75° C. followed by the drop wise addition of a solution of $Gd(NO_3)_3$ and $Eu(NO_3)_3$ (a total of 1 mmol) in 2 mL of methanol and a solution of 0.126 g of NaF (3 mmol) in 4 mL of water, while stirring. After 10 min, a solution of 0.576 g of $La(NO_3)_3$ (1.33 mmol) in 2 mL of methanol and a solution of 0.126 g of NaF (3 mmol) in 4 mL of water were added drop wise. After 1 hour, the particles were precipitated with ~50 mL of ethanol, isolated by centrifugation, washed three times with ethanol, followed by centrifugation and dried under vacuum. Percentages are relative to the total amount of $Ln^{3+}$ ions.

4—Preparation of citrate stabilized $LaF_3$—Gd:Eu(x%, x=5 and 10) core-shell nanoparticles: A solution of 2 g of citric acid in 35 mL of water was neutralized with ammonium hydroxide to a pH of 6 and heated to 75° C. followed by the drop wise addition of a solution of 0.443 g of $La(NO_3)_3$ (1 mmol) in 2 mL of methanol and a solution of 0.126 g of NaF (3 mmol) in 4 mL of water while stirring. After 10 min, a solution of $Gd(NO_3)_3$ and $Eu(NO_3)_3$ (a total of 1.33 mmol) in 2 mL of methanol and a solution of 0.126 g of NaF (3 mmol) in 4 mL of water were added drop wise. After 1 hour, particles were precipitated with ~50 mL of ethanol, isolated by centrifugation, washed three times with ethanol, followed by centrifugation and dried under vacuum. Percentages are relative to the total amount of $Ln^{3+}$ ions.

Results

Typical particle sizes were in the range of about 10 nm (about pH 5.08), about 15 nm (about pH 6.16), and about 20 nm (about pH 6.41) when 2-aminoethyl dihydrogen phosphate was used. With citrate, particle sizes were about 5 mn for core particles and about 6 for core-shell nanoparticles. The stated doping percentages are relative to the total amount of $Ln^{3+}$ in the core and are nominal.

Example 4

Lanthanide fluoride nanoparticles in positron therapy— Positron Emission Tomography (PET) is a well known technique for imaging of most tumors and relies upon the accumulation of positron emitting radionuclides such as $^{18}$F in tumor cells. $^{18}$F has been shown to have a radiotherapeutic effect in combating tumors.

Lanthanide trifluoride nanoparticles contain fluoride ions therefore they will be used to incorporate an arbitrary fraction of $^{18}$F (from $^{18}$F-enriched sodium fluoride) in the synthesis process. Doping a high proportion of the nanoparticles with $^{18}$F, will render the nanoparticles potent anticancer agents. as long as they are appropriately targeted. The main advantage of the nanoparticles is that a large concentration of positron emitters can thus be placed in the vicinity of tumors (using simple targeting strategies). This is otherwise extremely difficult to do using existing small molecules that incorporate one $^{18}$F species. This method will be adapted to treat many kinds of pathogens, for example, but not limited to viruses, and bacteria.

Example 5

Lanthanide phosphate, lanthanide fluoride, and lanthanide vanadate nanoparticles in neutron capture therapy (NCT).

NCT involves the use of stable isotopes that are used to capture epithermal neutrons resulting in localized cytotoxic radiation. Although traditional NCT therapy involved the use of boron clusters, gadolinium has the advantage that its neutron capture cross section is 66 times that of boron. In addition, $^{157}$Gd generates gamma rays and Auger electrons that are highly cytotoxic and possess stopping distances that extend beyond the dimensions of a single cell, thus avoiding the need to deposit the lanthanides inside the cell. Prior studies have determined that optimal gadolinium concentrations in tumors should approach 50-200 µg/g$^5$. The nanoparticle formulations of the present technology will allow delivery of significantly higher concentrations than those currently available. Gd-nanoparticle formulation will also be employed to function as both an imaging contrast agent and a drug, once irradiated. Clinicians will have the opportunity to determine maximal concentrations in target tissues before irradiating with neutrons. All types of pathogens will be treated with such an approach, using the appropriate target.

Example 6

Lanthanide phosphate, lanthanide fluoride, and lanthanide vanadate nanoparticles in radionuclide therapy and enhancement by high Z species. A wide variety of radionuclides are used in the treatment of tumors and pathogens today. Many of these radionuclides emit alpha particles, Auger electrons or beta particles of appropriate energies for soft tissue. In particular Auger electron emitters such as In-111 and beta emitters such as Y-90, I-131, Lu-177, and Re-188, all have specific applications in tumor therapy. Recently, it has been shown that the biological damage can be increased by as much as 300-400% in the presence of high Z-contrast agents. The approach involves the coadministration of a radionuclide with an agent designed to enhance the tissue damage through secondary interactions between the source radionuclide and high Z species. Such an approach relies on the partitioning of both components to the tumor tissue. In the case of the lanthanide phosphate, lanthanide fluoride, and lanthanide vanadate nanoparticles, the synthetic chemistry involved in sample preparation will be adapted to include a fraction of Lu-177. Moreover, isotopes of gadolinium will also be used as beta and gamma emitters. In either case, the background europium and gadolinium will function as the high Z species in the nanoparticle and will serve to magnify the biological damage to the surrounding tissue. This method will be adapted to target any type of pathogenic cell.

Conclusions

In conclusion, a paramagnetic nanoparticle additive, consisting of GdF$_3$ or a mixture of GdF$_3$ and LaF$_3$, has been synthesized and rendered highly water soluble through doping with La, and by the addition of either citric acid (GdF$_3$ particles) or positively charged ammonium groups (80/20 GdF$_3$/LaF$_3$). Relaxivities are such that around 10 nM of nanoparticles, water spin-lattice relaxation times to drop to around 125 ms, making them useful for decreasing repetition times in studies of proteins with very long relaxation times. The lack of direct interaction between nanoparticle and solute and the ease with which the nanoparticles can be removed from an NMR sample through centrifugation, suggests that these nanoparticles should be useful as relaxation agents in NMR studies. Thus, the nanoparticles possess high solubilities, confer high relaxation of the solvent at nanomolar concentrations, can be further modified to control solubility in specific solvents or prevent direct interactions with a given protein/macromolecule, and can be removed through ultracentrifugation, permitting the protein to be removed via the supernatant.

We have demonstrated that it is possible to modify nanoparticles with negatively and positively charged ligands, in addition to biotin. The nanoparticle surfaces can be easily modified to control solubility, and also avoid or direct interactions with the solute molecules or surrounding matrix. This becomes an advantage in MRI where functionalization of the particles confers retention time in a particular tissue. For example, coating the particles with polymers such as polyethylene glycol should confer lengthened retention time, while antibody coatings or small peptide coatings can be used to target specific cell receptors such as integrins. There are nearly limitless possibilities for functionalization for purposes of specific solubility, altered retention time and targeting.

The sizeable relaxivities observed for the GdF$_3$ nanopaticles, over a broad range of temperature and field strength shows great promise for these particles as MRI T$_1$ contrast agents and sensitivity agents. Relaxivities are orders of magnitude higher than conventional agents. Relaxation experiments on the supernatant after removal of the nanoparticles, revealed no residual presence of Gd$^{3+}$. Furthermore, exhaustive studies, in which the nanoparticles were left in solution for periods of days, then centrifuged, found no residual Gd$^{3+}$ in the supernatant, suggesting that lanthanide leaching is an extremely slow or nonexistent process, under in vitro conditions. Since the bulk of MRI relaxation and contrast agents are lanthanide chelates, and since lanthanide toxicities are always of concern, the lack of leaching may prove to be an equally useful attribute of this new class of relaxation agents, for MRI.

Currently X-ray imaging (Computed tomography or CT) makes use of iodinated compounds for scattering (contrast). The current scattering properties (based on atomic number density) of the LnF$_3$ nanoparticles are estimated to be twice that of the iodinated species on a mass concentration basis. Since leaching is weak or nonexistent, and since the particles can be further modified, there is great promise to develop the particles as contrast agents for CT scanning in addition to MRI.

The foregoing is a description of an embodiment of the technology. As would be known to one skilled in the art, variations that do not alter the scope of the technolgy are contemplated. For example, any lanthanide ion is contemplated, for example, Ho$^{3+}$, Dy$^{3+}$ LnPO$_4$, where Ln=La, Gd, Lu or Y, LnVO$_4$, oxides, LiLnF$_4$, and LaF$_3$. Further, any combination of any of the lanthanide ions in any ratio is contemplated, for example, but not limited to Ln$^{3+}$, LaPO$_4$, LnVO$_4$, Ln$_2$O$_3$, Ln$_2$(CO$_3$)$_3$, and Ln$_2$(C$_2$O$_4$)$_3$. Further, both core shell nanoparticles and core nanoparticles are contemplated. Still further, any other ligands that bind to lanthanides are contemplated. The anion could be, for example but not limited to PO$_4$$^{3-}$ or VO$_4$$^{3-}$. Further, any ligand that can render the nanoparticle soluble in an aqueous environment is also contemplated. For example, but not to be limiting, biotin is an effective ligand. Other ligands contemplated include, but are not limited to (overall) negatively charged ligands, e.g. citrate and H$_3$N$^+$CH$_2$CH$_2$OPO$_3$$^{2-}$, positively charged ligands and neutral ligands (the latter include a number of amino acids at physiological pH). Still further, the nanoparticles of the present technolgy would be expected to be effective X-ray contrast agents, such as in CT-scanning, based on their atomic (scattering densities). Similarly, the nanoparticles of the present technolgy would be useful in PET techniques and Gadolinium neutron capture therapy (GdNCT), as alternative to boron neutron capture therapy. Further, modification to the surface of ligands that are on the surface of the inorganic nanoparticle can be carried out to tune the biological properties. For example, but not limited to Eu$^{3+}$, Er$^{3+}$, and Nd$^{3+}$ doped nanoparticles with H$_3$N$^+$CH$_2$CH$_2$OPO$_3$$^{2-}$ as stabilizing ligands (the phosphate group binds to the surface of the nanoparticles and the amino group has been reacted with activated esters, for example, but not limited to activated esters with polyethylene glycol units).

The use of nanoparticles in tandem imaging is also contemplated. For example, at present, Positron Emission Tomography (PET scanning) utilizes radiolabeled metabolites to assess parameters such as blood flow, brain activity, and observing very small tumors, for example. With Na$^{18}$F, radioactive nanoparticles could readily be synthesized to permit simultaneous imaging by PET scanning. This would introduce a new functionality for PET scanning—namely the visualization of tissues (rather than cell activity).

It is also contemplated that GdF$_3$ nanoparticles can be affixed to small beads and incorporated into flow-through NMR tubing. A small frit or sieve can be used to prevent the beads from passing into the sample volume and the sample of the signal can be freely detected in the NMR receiver coil, with greatly enhanced sensitivity.

REFERENCES

[1] Young, S. W.; Qing, F.; Rubin, D.; Balkus, K. J.; Engel, J. S.; Lang, J; Dow, W. C.; Mutch, J. D.; Miller, R. A. *J. Magn. Reson. Imag.*, 1995, 5, 499-508.

[1] Andre, J. P.; Toth, E.; Fischer, H.; Seelig, A.; Macke, H. R.; Merbach, A. E. *Chem. Eur. J.*, 1999, 5, 2977-2983.

[1] Aime, S.; Botta, M.; Garino, E.; Crich, S. G.; Giovenzana, G.; Pagliarin, R.; Palmisano, G.; Sisti, M. *Magn. Reson. Med.* 2000, 6, 2609-2617.

[1] Lu, Z. R.; Parker, D. L.; Goodrich, K. C.; Wang, X. H.; Dalle, J. G.; Buswell, H. R. *Magn. Reson. Med.* 2004, 51, 27-34.

[1] Wiener, E. C.; Brechbiel, M. W.; Brothers, H.; Magin, R. L.; Gansow, O. A.; Tomalia, D. A.; Lauterbur, P. C. *Magn. Res Med.* 1994, 31, 1-8.

[1] Yan, G. P.; Bottle, S. E.; Zhuo, R. X.; Wei, L.; Liu, M. L.; Li, L. Y. *J. Bioactive and Comp. Polym.* 2004, 19, 453-465.

[1] Bulte, J. W. M. *J. Magnetism and Magnetic Materials* 2005, 289, 423-427.

[1] Moghimi, S. M.; Hunter, A. C. *Critical Reviews in Therapeutic Drug Carrier Systems* 2001, 18, 527-550.

[1] FernandezUrrusuno, R.; Fattal E.; Rodrigues, J. M.; Feger, J.; Bedossa, P.; Couvreur, P. *Journal of Biomedical Materials Research* 1996, 31, 401-408.

The invention claimed is:

1. An aqueous-soluble, lanthanide-rich nanoparticle composite, comprising:
   an inorganic, paramagnetic core consisting of at least one lanthanide ion selected from ions of Ce, Pr, Nd, Sm, Eu, Gd, Tb, Dy, Ho, Er, Tm, Yb, La, Lu, Y, and combinations thereof, and at least one anion selected from a halide, a phosphate, and a vanadate;
   at least one aqueous-soluble, organic ligand selected from citrate, biotin, amino acids, H$_3$N$^+$CH$_2$CH$_2$OPO$_3$$^{2-}$, and combinations thereof, wherein the at least one aqueous-soluble, organic ligand is bound to the inorganic, paramagnetic core; and
   at least one surface-modifying reagent that has been reacted with the at least one aqueous-soluble, organic ligand to form a surface-modifying reagent-aqueous soluble organic ligand reaction product.

2. The nanoparticle of claim 1 wherein said inorganic, paramagnetic core consists of at least two lanthanide ions.

3. The nanoparticle of claim 2 wherein said at least two lanthanide ions are Gd$^{3+}$ and La$^{3+}$.

4. The nanoparticle of claim 3 wherein said inorganic, paramagnetic core comprises gadolinium fluoride and lanthanum fluoride.

5. The nanoparticle of claim 4 wherein said inorganic, paramagnetic core comprises at least 50% gadolinium fluoride.

6. The nanoparticle of claim 5 wherein said inorganic, paramagnetic core comprises at least 80% gadolinium fluoride.

7. The nanoparticle composite of claim 1 wherein said at least one aqueous-soluble, organic ligand is either citrate or H$_3$N$^+$CH$_2$CH$_2$OPO$_3$$^{2-}$.

8. The nanoparticle of claim 7 wherein said inorganic, paramagnetic core consists of gadolinium fluoride and lanthanum fluoride.

9. The nanoparticle composite of claim 1 wherein the at least one lanthanide ion is selected from ions of Eu, Gd, Ho, and Er.

10. The nanoparticle composite of claim 9 wherein said at least one lanthanide ion is a gadolinium ion.

11. The nanoparticle composite of claim 10 wherein said at least one lanthanide ion is provided as gadolinium fluoride.

12. The nanoparticle composite of claim 11 wherein said at least one aqueous-soluble, organic ligand is citrate or H$_3$N$^+$CH$_2$CH$_2$OPO$_3$$^{2-}$.

13. The nanoparticle composite of claim 7 wherein said nanoparticle composite ranges in size from about 10 nm to about 150 nm in diameter.

14. The nanoparticle composite of claim 13 wherein said nanoparticle composite ranges in size from about 10 nm to about 20 nm.

15. The nanoparticle of claim 7 wherein said at least one aqueous-soluble, organic ligand is citrate.

16. The nanoparticle composite of claim 15 wherein said nanoparticle composite ranges in size from about 5 nm to about 10 nm.

17. The nanoparticle composite of claim 1 wherein said nanoparticle composite is a core shell nanoparticle.

18. The core shell nanoparticles of claim 17 wherein said nanoparticles consists of GdF$_3$:Eu(5%)-LaF$_3$ or LaF$_3$—Gd:Eu(5%).

19. The nanoparticle composite of claim 1 wherein said nanoparticle composite is a core nanoparticle.

20. An aqueous-soluble, lanthanide-rich nanoparticle composite, comprising:
- an inorganic, paramagnetic core consisting of at least one lanthanide ion selected from ions of Ce, Pr, Nd, Sm, Eu, Gd, Tb, Dy, Ho, Er, Tm, Yb, La, Lu, Y, and combinations thereof, and at least one anion selected from a halide, a phosphate, and a vanadate;
- at least one $H_3N^+CH_2CH_2OPO_3^{2-}$ ligand, wherein the at least one $H_3N^+CH_2CH_2OPO_3^{2-}$ ligand is bound to the inorganic, paramagnetic core; and
- at least one surface-modifying reagent selected from an activated ester, a polyethylene glycol, a peptide, an antibody, and combinations thereof, wherein the at least one surface-modifying reagent is bound to the at least one $H_3N^+CH_2CH_2OPO_3^{2-}$ ligand through an amine of the $H_3N^+CH_2CH_2OPO_3^{2-}$ ligand.

21. An aqueous-soluble, lanthanide-rich nanoparticle composite, consisting of:
- an inorganic, paramagnetic core consisting of at least one lanthanide ion selected from ions of Eu, Gd, Dy, Ho, Er, La, Lu, Y, and combinations thereof, and at least one anion selected from a halide, a phosphate, and a vanadate;
- at least one citrate ligand bound to the inorganic, paramagnetic core; and
- at least one antibody that has been reacted with the at least one citrate ligand to form an antibody-citrate ligand reaction product useful for targeting the nanoparticle for a desired NMR, MRI, CT, PET, or NCT application.

22. The nanoparticle composite of claim 1 wherein the at least one surface-modifying reagent is selected from a reagent capable of detecting a target, a non-biological polymer, and combinations thereof.

23. The nanoparticle composite of claim 1 wherein the at least one surface-modifying reagent is selected from an activated ester, a polyethylene glycol, a peptide, an antibody, and any combinations thereof.

24. An aqueous-soluble, lanthanide-rich nanoparticle composite, comprising:
- $GdF_3$ core;
- at least one citrate ligand bound to the $GdF_3$ core; and
- at least one antibody that has been reacted with the at least one citrate ligand to form an antibody-citrate ligand reaction product useful for targeting the nanoparticle for a desired NMR, MRI, CT, PET, or NCT application.

\* \* \* \* \*